United States Patent [19]

Anis

[11] Patent Number: 4,880,427
[45] Date of Patent: Nov. 14, 1989

[54] FLEXIBLE POSTERIOR CHAMBER LENS

[76] Inventor: Aziz Y. Anis, 9540 Firethorne La., Lincoln, Nebr. 68520

[21] Appl. No.: 201,388

[22] Filed: May 17, 1988

Related U.S. Application Data

[63] Continuation of Ser. No. 624,232, Jun. 25, 1984, abandoned.

[51] Int. Cl.<sup>4</sup> ............................................. A61F 2/16
[52] U.S. Cl. ...................................................... 623/6
[58] Field of Search ............................................. 623/6

[56] References Cited

U.S. PATENT DOCUMENTS

| | | | |
|---|---|---|---|
| 4,251,887 | 2/1981 | Anis | 3/13 |
| 4,363,143 | 12/1982 | Callahan | 3/13 |
| 4,377,329 | 3/1983 | Poler | 3/13 UX |
| 4,418,431 | 12/1983 | Feaster | 623/6 |
| 4,424,597 | 1/1984 | Schlegel | 623/6 |
| 4,494,254 | 1/1985 | Lopez | 3/13 |

FOREIGN PATENT DOCUMENTS

WO83/01568 5/1983 World Int. Prop. O. ............. 623/6

OTHER PUBLICATIONS

"Planned Extracapsular Cataract Extraction and the Insertion of the Lindstrom Centrex Style 20 Posterior Chamber Lens" by Richard L. Lindstrom, (Paper copyright by Richard L. Lindstrom, 1981), pp. 1-11.

Advertisement Brochure by Cilco, (6 pages), Oct. 1982, pp. 1, 4 & 6 cited, Cilco, Inc., 1616 13th Ave., Box 1680, Huntington, W.Va. 25717.

Published PCT Application (PCT/US82/01538), International Publication No. WO83/01568, May 11, 1983, Grendahl et al.

Primary Examiner—Ronald L. Frinks

[57] ABSTRACT

A flexible posterior chamber lens for implantation within an eye comprising a disc-shaped lens body having a front face, a convex rear face, and an outer peripheral edge. A flexible fixation element extends from the lens body and extends substantially around the entire peripheral edge of the lens body for engagement with substantial portion of the capsular equator when the lens is implanted. The convex rear face of the lens body engages the posterior capsule to stretch the same rearwardly so that cellular migration onto, and the opacification of the posterior capsule is substantially reduced or eliminated.

7 Claims, 4 Drawing Sheets

FLEXIBLE POSTERIOR CHAMBER LENS

This application is a continuation of application Ser. No. 624,232, filed 6-25-84, now abandoned.

BACKGROUND OF THE INVENTION

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view inasmuch as it cannot properly refract incident light rays. Aphakic correction may be accomplished in three ways:
(1) thick eye glasses worn in front of the eye;
(2) contact lenses worn on the eye; or
(3) artificial intraocular lens implant within the eye.

It is this latter procedure with which the instant invention is concerned.

The structure and procedure of installing an intraocular lens is very critical because the elements which make up the eye are extremely sensitive and subject to irreparable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feed extending between the ciliary processes and the base of the iris. The lens proved positionally unstable and resulted in unsatisfactory amounts of irritation.

U.S. Pat. No. 3,866,249 discloses a posteriorly positioned prosthetic lens which has a multiplicity of forwardly projecting prongs. During surgical implantation, the prongs are extended through the iris to anchor the lens in position. While this arrangement certainly maintains positional integrity, it, too, has distinct disadvantages. The great number of prongs extending through and over the iris promote undesirable irritational characteristics, and the number fixation points also have a tendency to distort the iris by pulling on it in numerous directions.

Finally, attention is directed to the lenses disclosed in U.S. Pat. Nos. 3,925,825; 3,913,148; and 3,922,728. Each of these patents teach a prosthetic lens structure which is, in one way or another, less than desirable in construction and use.

In an effort to remedy the problems associated with the prior art lens implants, applicant previously has been granted U.S. Pat. Nos. 4,143,427; 4,166,293 and 4,251,887. Other recent developments relating to implant lens may be found in U.S. Pat. Nos. 4,316,293 and 4,340,979.

A problem associated with the implantation of posterior chamber lenses is that opacification of the posterior capsule occurs through cellular migration onto the posterior capsule. A further problem associated with the prior art lenses is that the fixation elements do not engage substantially the entire capsular equator when the lens is implanted.

Therefore, it is a principal object of the invention to provide an improved flexible posterior chamber lens.

A further object of the invention is to provide a posterior chamber lens which is provided with a convex rear face which engages the posterior capsule to stretch the same rearwardly so that cellular migration onto, and the opacification of the posterior capsule is substantially reduced or eliminated.

A further object of the invention is to provide a posterior chamber lens including a flexible holding means which engages substantially the entire capsular equator when the lens is implanted.

Still another object of the invention is to provide a flexible posterior chamber lens which is of one-piece construction.

These and other objects will be apparent to those skilled in the art.

SUMMARY OF THE INVENTION

A flexible posterior chamber lens is provided which includes a disc-shaped lens body having a front face, a convex rear face, and an outer peripheral edge. The convex rear face of the lens body engages the posterior capsule to stretch the same rearwardly so that cellular migration onto, and the opacification of the posterior capsule is substantially reduced or eliminated. A flexible holding means is formed with the lens body and extends therefrom for engagement with substantially the entire capsular equator when the lens is implanted. In each of the embodiments, the flexible holding means has at least one support means which separates a fixation member from the lens body by a space. In one form of the invention, a pair of closed kidney-shaped loops are provided on the lens body. In another form of the invention, a support post extends radially outwardly from the lens body and has a pair of oppositely disposed arcuate fixation elements extending therefrom around substantially the entire peripheral edge of the lens body. In yet another form of the invention, a support post extends radially outwardly from the lens body and has a pair of fixation elements extending around substantially the entire peripheral edge of the lens body with the ends of the fixation elements being secured to the lens body. In yet another embodiment of the invention, a single fixation element extends from a support post around substantially the entire peripheral edge of the lens body. In still another embodiment of the invention, a pair of substantially semi-circular fixation elements extend around substantially the entire peripheral edge of the lens body.

DESCRIPTION OF THE PREFERRED EMBODIMENTS

Figure 3:
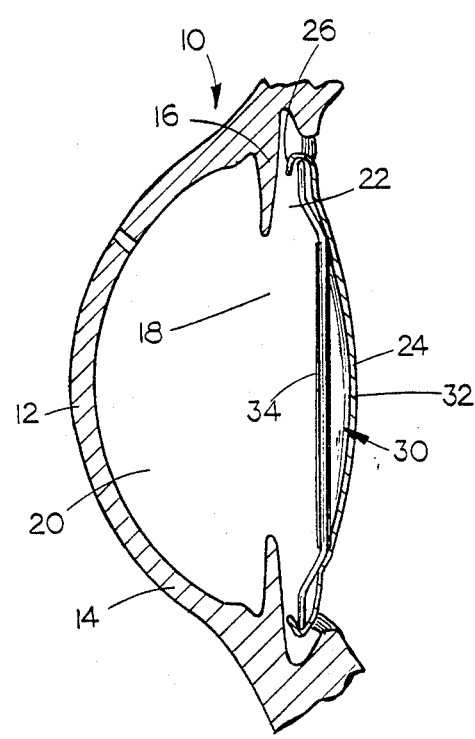
FIG. 3 is a sectional view illustrating the lens of FIG. 1 implanted in the posterior chamber.

In FIG. 3, the numeral 10 refers to an eye, after cataract removal by surgical procedure. Eye 10 includes a cornea 12 which merges into an opaque protective covering 14 called sclera. Behind the cornea 12 is the iris 16 which defines a central opening 18 known as the pupil. The iris 16 comprises a muscular diaphragm-like element capable of expansion and contraction to control the amount of light passed therethrough. The iris divides the internal chamber of the eye into two chambers, the anterior chamber 20 and the posterior chamber 22. The natural crystalline lens of the eye would be located in the posterior chamber 22 adjacent the pupil 18. After the natural lens has been surgically removed, a relatively flattened posterior capsule or membrane 24 remains. Normally, a small part of the anterior capsule also remains and is referred to generally by the reference numeral 26 in FIG. 3. In the prior art implants, the posterior capsule 24 is not in close engagement with the lens implant and cells tend to migrate onto the posterior capsule which causes the opacification of the posterior capsule.

Figure 1:
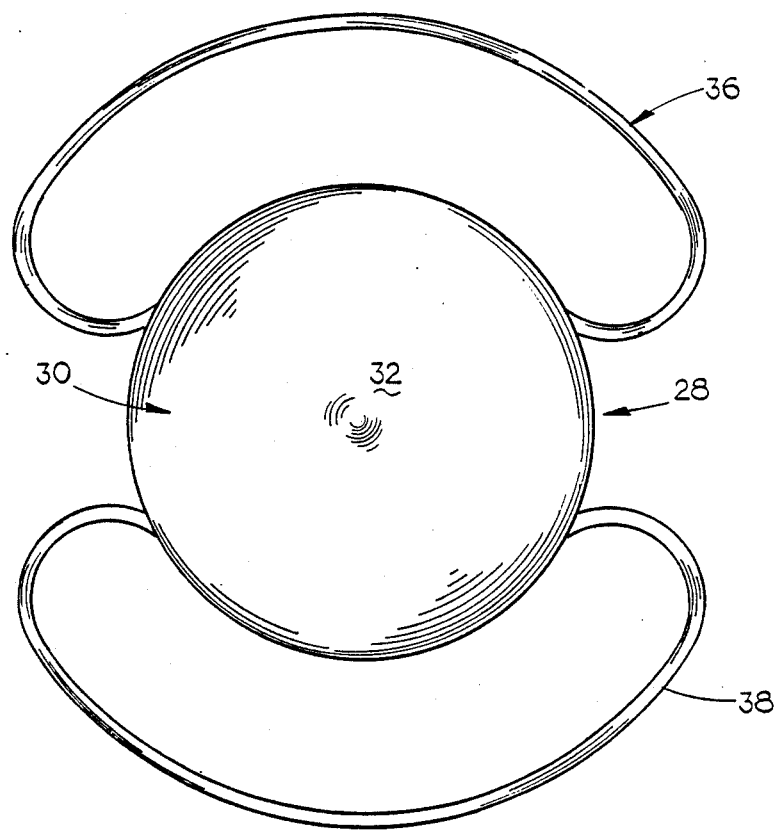
FIG. 1 is a plan view of one form of the invention.
Figure 2:
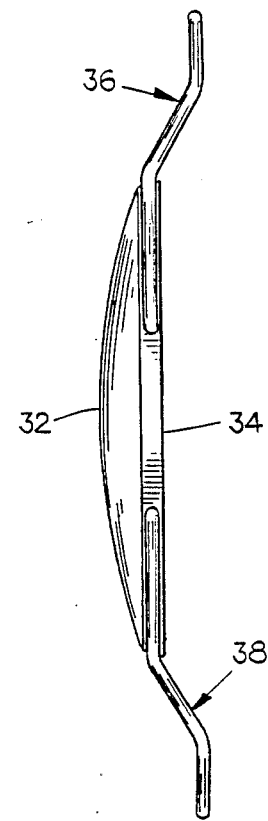
FIG. 2 is a side view of the lens of FIG. 1.

FIGS. 1 and 2 illustrate one form of the lens structure which is referred to generally by the reference numeral 28. Lens 28 comprises a disc-shaped lens body 30 having a convex rear or posterior face 32 and a plano front or anterior face 34. If desired, the front face 34 could also be of convex configuration. Fixation elements 36 and 38 are integrally formed with lens body 30 and extend from the peripheral thereof in the manner illustrated in FIG. 1. As seen in FIG. 2, the outer end portions of fixation elements 36 and 38 dwell in a plane forwardly of the face 34. Although the design of the fixation element or elements varies from embodiment to embodiment, all of the fixation elements are disposed so that the outer ends thereof engage a substantial portion of the capsular equator when the lens is implanted.

Figure 4:
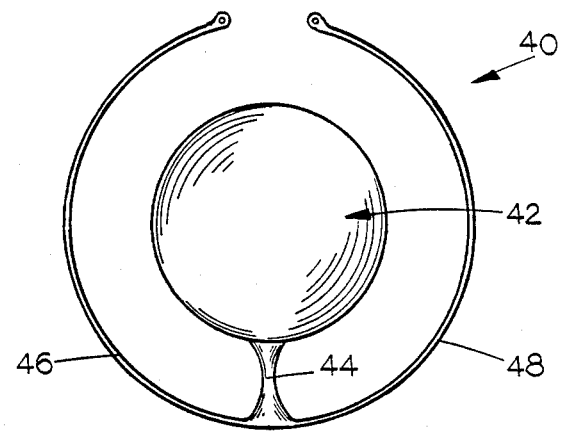
FIG. 4 is a plan view of a modified form of the invention.

FIG. 4 illustrates a modified form of the lens which is designated by the reference numeral 40. Lens 40 includes lens body 42 which may be plano-convex or bi-convex as in lens 28. Support post 44 extends radially outwardly from lens body 42 and has a pair of fixation elements 46 and 48 integrally formed with the support post and extending therefrom around substantially the entire peripheral edge of the lens body 42 in a spaced-apart relationship each fixation element having one free end.

Figure 5:
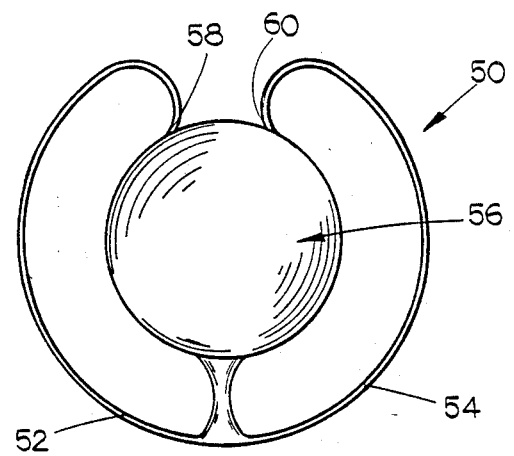
FIG. 5 is a plan view of still another modified form of the invention.
Figure 6:
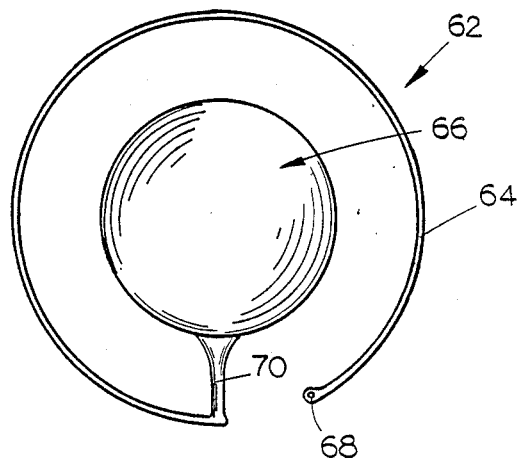
FIG. 6 is a plan view of still another modified form of the invention.

FIG. 5 illustrates a lens 50 which is substantially identical to lens 40 except that the fixation elements 52 and 54 are joined or are secured to the lens body 56 at 58 and 60.

The numeral 62 refers to a further embodiment of the lens in FIG. 5 wherein a single fixation element 64 extends from the lens body 66 so that the end 68 of the fixation element 64 terminates closely adjacent the support post 70 and thus leaving one free end of the fixation element.

Figure 8:
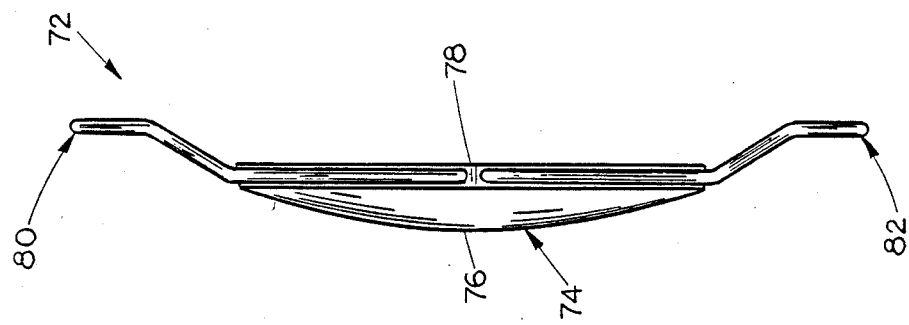
FIG. 8 is a side view of the lens of FIG. 7.
Figure 7:
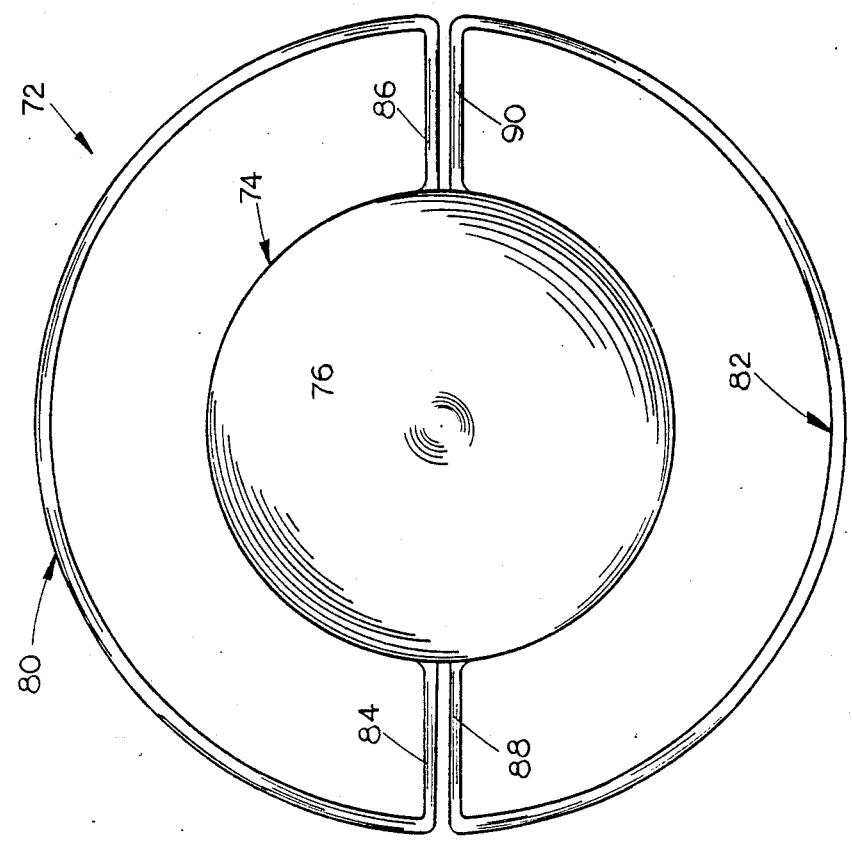
FIG. 7 is a plan view of yet another modified form of the invention.

FIGS. 7 and 8 illustrate yet another lens which is referred to by the reference numeral 72. Lens 72 comprises a disc-shaped lens body 74 having a convex rear or posterior face 76 and a plano front or anterior face 78. If desired, the anterior face 76 could also be of convex configuration. Fixation elements 80 and 82 are integrally formed with lens body 74 and are substantially semi-circular shaped in a plan view so that the fixation elements extend substantially around the entire peripheral edge of the lens as illustrated in FIG. 7. Fixation element 80 includes support posts 84 and 86 extending from the lens body while fixation element 82 includes support posts 88 and 90 extending from the lens body. The support posts 84, 86 and 88, 90 extend anteriorly or forwardly from the lens body as illustrated in FIG. 8 so that the outer end portions of the fixation elements dwell in a plane forwardly of the face 76 as in the other embodiments. If desired, the support posts 84, 86 and 88, 90 could extend forwardly at right angles to the face 78 and thence outwardly to enable the outer end portions of the fixation elements to dwell in a plane forwardly of the face 76.

Figure 9:
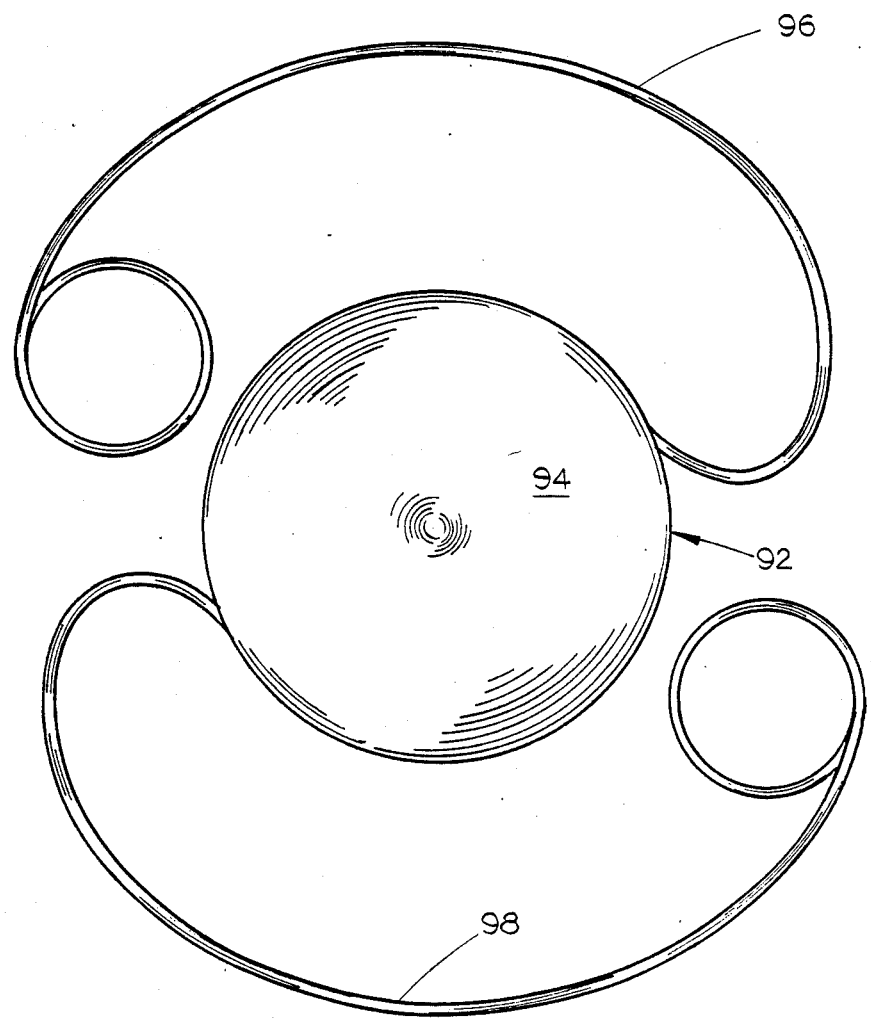
FIG. 9 is a plan view of still another modified form of the invention.

FIG. 9 illustrates still another lens which is referred to by the reference numeral 92. Lens 92 comprises a disc-shaped lens body 94 having a convex rear or posterior face and a plano-front or anterior face. If desired, the anterior face could also be of convex configuration. Fixation elements 96 and 98 are flexible and extend from opposite points on lens 94 as seen in the drawings. Each of the fixation elements are curved upon themselves as seen in FIG. 9 and when compressed, will extend substantially around the entire peripheral edge of the lens.

In all of the lens embodiments described hereinabove, the lens body and the fixation element or elements are preferably of unitary one-piece construction. Preferably, the lens material and the fixation elements are comprised of PMMA material. In the embodiment of FIG. 9, the loops could be comprised of polypropylene if so desired.

Further, all of the fixation elements are designed so that fixation element or elements will engage substantially the entire capsular equator when the lens is implanted to aid in properly positioning the lens and to aid in maintaining the lens in position after implantation. In each of the lens embodiments, the convex rear face thereof engages the posterior capsule 24 to stretched the same rearwardly so that close engagement is achieved therebetween to prevent cellular migration onto the posterior capsule thereby preventing opacification of the posterior capsule.

Thus it can be seen that the invention accomplishes at least all of its stated objectives.

I claim:

1. A flexible posterior chamber lens, for implantation within an eye, comprising:
    a disc-shaped lens body having a front face, a convex rear face, and an outer peripheral edge;
    flexible holding means secured to and extending around substantially the entire peripheral edge of said lens body and having an outer end disposed forwardly of said convex rear face in a plane perpendicular to the optical axis of said lens body so that said holding means will engage substantially the entire capsular equator when the lens is implanted to reduce cellular migration into and the opacification of the posterior capsule;
    said lens body and flexible holding means being made of PMMA;

said holding means and said lens body are of one-piece construction;
said holding means including only one post member radially extending from the lens body and at least one fixation means;
said fixation means being entirely separated from said lens body by said one support post member.

2. A flexible posterior chamber lens, for implantation within an eye, comprising:
a disc-shaped lens body having a front face, a convex rear face, and an outer peripheral edge;
flexible holding means secured to and extending around substantially the entire peripheral edge of said lens body and having an outer end disposed forwardly of said convex rear face and in a plane perpendicular to the optical axis of said lens body so that said holding means will engage substantially the entire capsular equator when the lens is implanted to reduce cellular migration into the opacification of the posterior capsule;
said holding means including two fixation elements having outer ends disposed forwardly of said convex rear face and in a plane perpendicular to the optical axis of said lens, for engaging substantially the entire capsular equator when the lens is implanted;
said holding means and said lens body are of one-piece construction;
said holding means including a support post extending radially outwardly from said lens body, a first fixation element extending from said support post around substantially one-half of the peripheral edge of said lens body, a second fixation element extending from said support post, opposite to said first fixation element, around substantially one-half of the peripheral edge of said lens body;
said first and second fixation elements being integrally formed with said lens body through said support post.

3. The lens of claim 2 wherein said first and second fixation elements have free ends spaced from each other.

4. The lens of claim 2 wherein the other ends of said fixation elements are connected to said lens body.

5. A flexible posterior chamber lens for implantation within an eye, comprising:
a disc-shaped lens body having a front face, a convex rear face, and an outer peripheral edge;
flexible holding means secured to and extending around substantially the entire peripheral edge of said lens body and having an outer end disposed forwardly of said convex rear face in a plane perpendicular to the optical axis of said lens body so that said holding means will engage substantially the entire capsular equator when the lens is implanted to reduce cellular migration into and the opacification of the posterior capsule;
said holding means including at least one fixation means having an outer end disposed forwardly of said convex rear face and in a plane perpendicular to the optical axis of said lens, for engaging substantially the entire capsular equation when the lens is implanted;
said holding means and said lens body being of one-piece construction;
only one support post extending radially and one end of a fixation element extending from said support post around substantially the entire peripheral edge of said lens body;
said fixation element having one free end.

6. A flexible posterior chamber lens, for implantation within an eye, comprising:
a disc-shaped lens body having a front face, a convex rear face, and an outer peripheral edge;
flexible holding means secured to and extending around substantially the entire peripheral edge of said lens body and having an outer end disposed forwardly of said convex rear face in a plane perpendicular to the optical axis of said lens body, so that said holding means will engage substantially the entire capsular equator when the lens is implanted to reduce cellular migration into and the opacification of the posterior capsule;
said holding means including at least one fixation means having an outer end disposed forwardly of said convex rear face and in a plane perpendicular to the optical axis of said lens, for engaging substantially the entire capsular equator when the lens is implanted;
said holding means and said lens body are of one-piece construction;
said holding means including a pair of generally semi-circular shaped loops.

7. A method of surgery comprising the steps: of
removing a cataract by surgical procedure; and
inserting a flexible, PMMA lens implant of one-piece construction having a convex rear face;
said implant having a holding means including a fixation means in a position where the fixation means engages substantially the entire capsular equator in the capsular bag with said convex rear face of the implant being held rearwardly by a curved portion of the holding means to provide sufficient contact with the posterior capsule to stretch the same rearwardly enough to prevent cellular migration into the posterior capsule and prevent opacification of the posterior capsule.

* * * * *